United States Patent [19]

Goodall et al.

[11] Patent Number: 4,880,546
[45] Date of Patent: Nov. 14, 1989

[54] RECOVERY OF TRANSITION METALS FROM AQUEOUS SOLUTIONS

[75] Inventors: Brian L. Goodall, Akron, Ohio; Paulus A. M. Grotenhuis, Amsterdam, Netherlands

[73] Assignee: Shell Oil Company, Houston, Tex.

[21] Appl. No.: 285,464

[22] Filed: Dec. 16, 1988

[30] Foreign Application Priority Data

Dec. 17, 1987 [GB] United Kingdom ............... 8729446

[51] Int. Cl.$^4$ ............................................ B01D 17/00
[52] U.S. Cl. ...................................... 210/699; 558/85; 568/454
[58] Field of Search ............... 210/699, 698, 663, 661, 210/685, 674, 638, 675, 651; 558/85; 568/455, 454, 451

[56] References Cited

U.S. PATENT DOCUMENTS

| | | | |
|---|---|---|---|
| 3,882,018 | 5/1975 | Depree | 210/674 |
| 3,957,504 | 5/1976 | Win-Sow Ho et al. | 210/638 |
| 3,966,595 | 6/1976 | Gosser | 210/651 |
| 4,265,769 | 5/1981 | Dingwall et al. | 210/699 |

*Primary Examiner*—Frank Sever

[57] ABSTRACT

Process for the recovery of a transition metal from an aqueous solution containing a complex of the transition metal with a cyclic phosphite by hydrolyzing the cyclic phosphite, contacting the hydrolysis reaction mixture with a compound forming a water-stable complex with the transition metal, extracting the reaction mixture thus formed with an organic extraction agent for the water-stable complex and separating an organic extract phase containing the transition metal from an aqueous raffinate phase. The process is particularly suitable for the recovery of the Rh or Co from spent hydroformylation catalysts and of Pd from spent carbonylation catalysts.

14 Claims, No Drawings

RECOVERY OF TRANSITION METALS FROM AQUEOUS SOLUTIONS

FIELD OF THE INVENTION

The invention relates to a process for the recovery of a transition metal from an aqueous solution containing a complex of said transition metal with a cyclic phosphite having a bridgehead phosphorus atom linked to three oxygen atoms at least two of which form together with the bridgehead phosphorus atom part of a ring, said cyclic phosphite having a hydroxymethyl group linked to a ring carbon atom, one or more of the hydrogen atoms in the cyclic phosphite optionally being substituted.

BACKGROUND OF THE INVENTION

The aqueous solutions described hereinbefore become available in the process described in European patent application No. 0,206,377. This known process concerns extraction of a transition metal from an organic medium by contacting it with an aqueous phase in the presence of a cyclic phosphite of the type described hereinbefore, so as to obtain an aqueous extract phase containing said metal. Such transition metals include all the noble and non-noble metals of Group VIII of the Periodic Table of the Elements. This process is very suitable when the organic medium contains rhodium or cobalt, in complex combination with a compound of trivalent phosphorus, which rhodium or cobalt has been used as a catalyst component for the preparation of aldehydes by hydroformylation of an ethylenically unsaturated compound with carbon monoxide and hydrogen in the presence of a solvent. The aldehydes are meant to include herein the corresponding alcohols which may have been formed by reduction of the aldehydes. Although the amounts of rhodium required for the hydroformylation are generally very small, rhodium and the compounds thereof are so expensive that the catalyst should be recovered completely or practically completely. Moreover, such a recovery method should be simple. Therefore, attempts have been made to recover rhodium from said aqueous solutions. The aqueous solution may be separated by means of distillation at sub-atmospheric pressure at a relatively low temperature into a distillate fraction containing water and a residual fraction containing rhodium in complex combination with the cyclic phosphite. The rhodium in complex combination with the cyclic phosphite present in the residual fraction may be reused for hydroformylation, but a disadvantage thereof is that the aldehydes formed usually do not have a sufficiently high linearity. The linearity is defined herein as the percentage of n-aldehydes in the mixture of aldehydes formed. It is therefore usually more attractive to convert the complex of rhodium with the cyclic phosphite into a hydroformylation catalyst comprising rhodium in complex combination with a phosphine or with a phosphite other than the said cyclic phosphite. According to European patent application No. 0,206,377, this may be carried out by burning the rhodium-cyclic phosphite complex present in said residual fraction with formation of rhodium oxide, which, in turn, is converted in a known manner into a hydroformylation catalyst. This known process for the recovery of rhodium is not very simple, distillation, burning and preparation of a hydroformylation catalyst starting from rhodium oxide being involved. Moreover, distillation of water requires much energy.

It is an object of the present invention to recover the transition metal in a very simple manner.

A further object is to recover the transition metal without having to distill off water.

Another object is to recover the transition metal completely or practically completely.

Still another object is to recover the transition metal in complex combination with any desired ligand.

SUMMARY OF THE INVENTION

This invention provides a process for the recovery of a transition metal from an aqueous solution containing a complex of said transition metal with a cyclic phosphite having a bridgehead phosphorus atom linked to three oxygen atoms at least two of which form together with the bridgehead phosphorus atom part of a ring, said cyclic phosphite having a hydroxymethyl group linked to a ring carbon atom, one or more of the hydrogen atoms in the cyclic phosphite optionally being substituted, which process comprises:

(a) hydrolyzing the cyclic phosphite in said complex, (b) contacting the reaction mixture obtained in (a) with a compound forming a water-stable complex with said transition metal, (c) contacting the reaction mixture obtained in (b) with a organic extraction agent for said water-stable complex, thus forming an organic extract phase containing at least a portion of said transition metal, and an aqueous raffinate phase, and (d) separating the organic extract phase containing at least a portion of said transition metal from the aqueous raffinate phase.

DESCRIPTION OF THE PREFERRED EMBODIMENTS

The simplicity of the process according to the present invention resides in the facts that the cyclic phosphite is readily hydrolyzed at elevated temperatures and that the water-stable complex is almost instantaneously formed and easily extracted by the organic extraction agent.

Any cyclic phosphite of the type defined hereinbefore may be used. According to a preferred embodiment of the present invention the cyclic phosphite is bicyclic and has the general formula I:

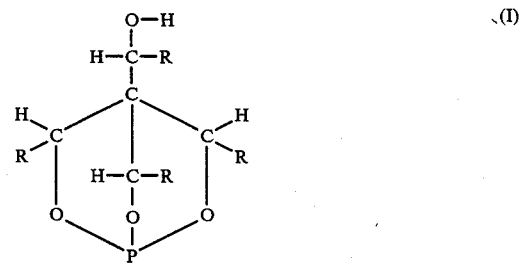

in which each R individually represents a hydrogen atom or an alkyl group having not more than three carbon atoms. Preferably, each R represents a methyl group, or, more preferably, a hydrogen atom. Very good results have been obtained with 4-hydroxymethyl-2,6,7-trioxa-1-phosphabicyclo[2,2,2]octane, this compound and its complexes with transition metals being highly soluble in water.

Alternatively, the cyclic phosphate is monocyclic and has the general formula II:

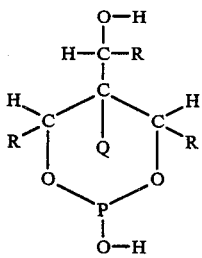

(II)

in which each R has the same meaning as in formula I and Q represents a hydrogen atom or an alkyl group having not more than three carbon atoms or a group of the general formula:

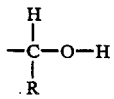

in which R has the same meaning as in formula I. The group:

in the general formula II is also meant to include the tautomeric structure:

Complete hydrolysis of a bicyclic phosphite results in the formation of ortho-phosphorus acid —$H_3PO_3$— and an alcohol having four hydroxy groups per molecule and having the general formula III:

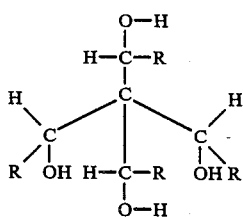

(III)

in which R has the same meaning as in the general formula I.

Complete hydrolysis of a monocyclic phosphite results in the formation of ortho-phosphorus acid and an alcohol having three hydroxy groups per molecule and having the general formula IV

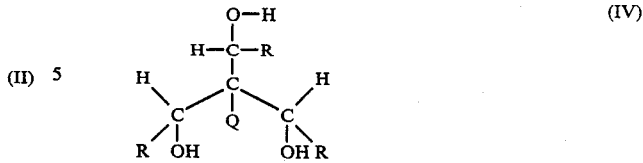

in which R and Q have the same meaning as in the general formula II.

Most of the ortho-phosphorus acid and the alcohols of the general formula III and IV will be found in the aqueous raffinate phase separated in step (c).

The cyclic phosphite in the complex is readily hydrolyzed and in some cases it will therefore be sufficient to simply heat the starting aqueous solution to a temperature in the range of, for example, 25° C. to 150° C., in particular 50° C. to 125° C. In most cases, however, hydrolysis is carried out at an enhanced rate by the presence of a hydrolysis-promoting agent. According to a preferred embodiment, a hydrolysis catalyst is present, in particular a protonic acid. Suitably, an equivalent ratio complex to protonic acid in the range of from 0.001 to 50 is applied. Very good results have been obtained with p-toluenesulfonic acid. Other examples of suitable protonic acids are sulfuric acid, methanesulfonic acid, benzenesulfonic acid, chloroacetic acid and trichloroacetic acid.

Alternatively, the hydrolysis in step (a) is carried out in the presence of a basic compound, for example, a hydroxide of an alkali metal or of an alkaline earth metal. Examples of such hydroxides are sodium hydroxide, potassium hydroxide and calcium hydroxide.

Upon hydrolysis of the cyclic phosphite-metal complex, the water-stable complex with the transition metal is formed. In this context, water-stable implies that the complex undergoes essentially no decomposition under the conditions chosen for steps (a), (b) and (c). Eligible compounds forming such complexes are compounds of trivalent phosphorus, for example tertiary phosphines and tertiary phosphites with tertiary phosphines being preferred. Examples of tertiary phosphines are triarylphosphines, trialkylphosphines and mixed arylalkylphosphines, and further mixed aryl-aryloxyphosphines, mixed aryl-alkoxy-phosphines and mixed alkyl-alkoxyphosphines. Examples of tertiary phosphites are triaryl phosphites and trialkyl phosphites. The aryl group can be, for example, a phenyl or naphthyl group and can be substituted with, for example, an alkyl group having in the range of from 1 to 20 carbon atoms. Examples of suitable compounds are triphenylphosphine, triphenyl phosphite, tri-p-tolylphosphine, tri-p-tolyl phosphite, tri-alpha-naphthylphosphine, tri-alpha-naphthyl phosphite, tri-p-biphenyl phosphite, tri-p-biphenylphosphine, tri-o-chlorophenyl phosphite and tri-o-chlorophenylphosphine. Examples of other suitable ligands are those represented by formula (V):

(V): $R_nPPh_{3-n}$ (V)

wherein R represents a branched alkyl group or a cycloalkyl group, n represents an integer of 1 or 2 and Ph represents phenyl. The use of such ligands is described in European patent application No. 0028378. Other examples of suitable ligands are triarylphosphines which have an electron-withdrawing substituent on an aryl ring; such ligands are described in European patent application No. 0102341.

Other compounds forming a water-stable complex with the transition metal are nitrogen bidentate ligands of the general formula:

wherein X and Y represent the same or different organic bridging groups, each bridging group having three or four atoms in the bridge wherein at least two atoms of each bridge are carbon atoms. The nitrogen bidentate ligand is preferably 2,2'-bipyridyl or a substituted derivative thereof, or 1,10-phenanthroline or a substituted derivative thereof.

Preferred compounds forming a water-stable complex with the transition metal are compounds of the general formula:

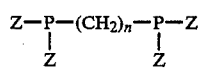

in which each Z individually represents a substituted or unsubstituted hydrocarbon group and n is an integer in the range of from 1 to 6. Suitably, the hydrocarbon group is an aryl group, for example a phenyl group.

Suitably, the compound forming a water-stable complex with the transition metal is selected according to the envisaged end use of the resulting complex. The end use will frequently be in the area of homogeneous catalysis, such as hydroformylation of olefins and carbonylation of olefins. For example, if rhodium is being recovered for olefin hydroformylation, triphenylphosphines can be suitably employed, whereas, if cobalt is recovered for hydroformylation, trialkylphosphines would be preferred.

Steps (a) and (b) may be carried out separately, but it is a preferred feature of the present invention that they can be carried out simultaneously. In such a case the cyclic phosphite in the complex is hydrolyzed in the presence of a compound forming a water-stable complex with a transition metal.

Any organic extraction agent for said complex can be used in step (c) provided that upon contacting this extraction agent with the reaction mixture obtained in step (b), an organic extract phase and an aqueous raffinate phase are formed. Suitably, such organic extraction agents are hydrocarbon extraction agents, which may be aromatic, for example benzene, toluene, the three xylenes and ethylbenzene, or aliphatic, for example hexane, heptane, octane, or cycloaliphatic, for example cyclohexane. Hydrocarbon fractions can be used such as for example, a kerosine fraction. Other examples of suitable solvents are acetophenone, benzonitrile, cyclohexanone, ethers such as diethyl ether, methyl isobutyl ether and anisole, and chlorinated hydrocarbons such as chlorobenzene and methylene chloride. Mixtures of such extraction agents may be used, for example, mixtures of toluene and cyclohexane. Suitably, in step (c) a volume ratio aqueous solution to organic extraction agent in the range of from 0.1 to 10 is used. If desired, step (c) may be carried out in the presence of a phase transfer agent the purpose of which is to enable the transition metal to cross smoothly into the organic extract phase. The phase transfer agent suitably contains polar and non-polar moieties to provide affinity for both aqueous and organic phases. Examples of phase transfer agents are sodium dodecyl sulfate and cetyltrimethylammonium bromide. A molar ratio phase transfer agent to transition metal in the range of from, for example, 100:1 to 1:1 can be used.

Steps (b) and (c) may be carried out as two consecutive steps. However, in a preferred embodiment of the present invention these two steps are carried out simultaneously. It is particularly preferred to carry out steps (a), (b) and (c) simultaneously, in which case the hydrolysis is carried out in the presence of a compound forming a water-stable complex with the transition metal and of an organic extraction agent for said water-stable complex. This preferred embodiment excels in simplicity, only one step instead of three being involved.

It is a feature of the present invention that the starting aqueous solution may have a very low concentration of transition metal, yet the organic extract phase contains a very high portion of the transition metal. Favorable concentrations of the transition metals to be recovered are in the range of from about 0.01 mmol/l to about 100 mmol/l, but concentrations below about 0.01 mmol/l or above about 100 mmol/l are not excluded.

The transition metal is preferably a metal, and, in particular, a noble metal from Group VIII of the Periodic Table of the Elements, i.e. ruthenium, rhodium, palladium, osmium, iridium and platinum. Among the noble metals, preference is given to palladium and rhodium. Among the other metals from Group VIII, cobalt is preferred. Other examples of transition metals are vanadium and manganese. The presence of two or more than two transition metals in the starting solution is not excluded.

The following Examples further illustrate the invention. The phosphite used in the Examples was 4-hydroxymethyl-2,6,7-trioxa-1phosphabicyclo[2,2,2]octane, referred to in the Examples as "POP". The steps have been given numbers which correspond to those of the steps described hereinbefore. The selectivity to a certain compound, expressed in a percentage, is defined as $100 \times a:b$ in which "a" is the amount of starting compound that has been converted into that certain compound and "b" is the total amount of starting compound that has been converted.

The invention is further described by the following examples which are intended to be illustrative and are not to be construed as limiting the scope of the invention.

EXAMPLE 1

Recovery of Rh-containing hydroformylation catalyst

A (300 ml) stainless steel autoclave equipped with a mechanical stirrer, a gas inlet tube, a thermocouple pipe and a pressure indicator was charged with 1-decene (1.0 mol), N,N-dimethylacetamide (25 ml), triphenylphosphine (0.02 mol) and rhodium-hydrido-carbonyl-tris(triphenylphosphine) (0.02 mmol), the molar ratio Rh:phosphine:1-decene being 1:1000:50000. The autoclave was flushed with an equimolar mixture of hydrogen and carbon monoxide and then pressurized with this mixture to 2 bar. The reaction mixture was heated to 75° C. while maintaining a pressure of 2 bar. After a total reaction time of 6 hours, the mixture was worked up by distillation at sub-atmospheric pressure. The hydroformylation reaction rate amounted to 7500 mol per gram-atom rhodium per hour, with a selectivity to undecanal of 86%. The distillation residue which was obtained consisted of heavy ends, a complex of rhodium and triphenylphosphine and free triphenylphosphine.

To this residue a solution of POP (0.4 mmol) in dimethylacetamide (15 ml) was added and the mixture was stirred for 2 hours. Then, water was added (20 ml) and after stirring and settling the phases were separated.

The aqueous layer was put into a separate autoclave. To this solution was added a trace of para-toluenesulfonic acid (0.05 g) and a solution of triphenylphosphine (0.02 mol) in 20 ml toluene. The autoclave was flushed with an equimolar mixture of $H_2$ and CO and then pressurized with this mixture to 5 bar. The mixture was subsequently heated to 90° C. After 3 hours reaction time (simultaneous application of steps 1, 2 and 3) the heating was stopped and the mixture was allowed to cool to ambient temperature. The organic extract phase (upper layer) was then separated from the aqueous raffinate phase (step d)). Analysis of the aqueous raffinate phase revealed it to be free of rhodium thus demonstrating that all the rhodium had dissolved in the organic extract phase in the form of a Rh/triphenylphosphine complex. This solution was reused in a hydroformylation of 1-decene which was carried out in the manner described hereinbefore in this Example. The hydroformylation reaction rate amounted to 7300 mol per gram-atom rhodium per hour, with a selectivity to undecanol of 87%.

EXAMPLE 2

Recovery of Rh-containing hydroformylation catalyst

To an aqueous stream (obtained after the hydroformylation of 1-decene according to the procedure as described in Example 1) containing 0.02 mmol of a Rh/POP complex was added 50 ml toluene, 0.40 mmol 1,5-di(diphenylphosphino)pentane and 0.1 g p-toluenesulfonic acid. This mixture was heated at 75° C. under 5 bar $H_2$/CO pressure during 3 hours (simultaneous application of steps (a), (b) and (c)). After cooling and depressurizing, the phases were separated (step d). The organic extract phase was washed with water (20 ml) to remove last traces of acid. Rhodium analysis of the aqueous raffinate phase showed that the extraction efficiency was 96%. The catalyst, dissolved in the organic extract phase was reused in a hydroformylation experiment of 1-decene. At a temperature of 90° C. and a pressure of 2 bar, the selectivity to undecanal amounted to 82% with a reaction rate of 5000 mol per gram-atom rhodium per hour.

EXAMPLE 3

Recovery of Co-containing hydroformylation catalyst

A mixture of linear $C_{12}$-$C_{14}$- olefins having non-terminal carbon carbon double bonds was hydroformylated in the presence of a cobalt-containing catalyst, followed by distillation of the reaction mixture, yielding a residue of heavy ends containing spent catalyst. To this residue 2-ethylhexanol (69 g) and toluene (40 g) were added and finally so much POP that a POP/cobalt molar ratio of 15 was obtained. After stirring for 1 hour, water was added (400 ml). After phase separation an aqueous layer was obtained containing a cobalt/POP complex. To this solution 0.5 g of potassium hydroxide, toluene (100 g) and phenyldilaurylphosphine was added (molar ratio Co:phosphine=1:1). This mixture was heated at 75° C. at 50 bar $H_2$/ CO pressure while stirring (simultaneous application of steps (a), (b) and (c)). After 4 hours, the mixture was cooled to ambient temperature, the autoclave was depressurized and discharged. The mixture was put into a separatory funnel. After 0.5 h settling time the layers were separated (step 4) yielding an organic extract phase containing a cobalt/phosphine complex. Analysis of the aqueous raffinate phase showed that 80% of the cobalt had been extracted into the organic extract phase.

This recovered catalyst was reused in the hydroformylation of 1-decene. At a reaction temperature of 200° C. and a pressure of 70 bar the selectivity to undecanols amounted to 80%.

EXAMPLE 4

Recovery of Pd-containing carbonylation catalyst

Ethene was carbonylated as follows, using a palladium catalyst in the presence of methanol to yield methyl propionate. The autoclave described in Example 1 was charged with 1 mmol palladium acetate, 50 mmol triphenylphosphine, 15 mmol methanesulfonic acid, 50 g methanol and 100 g methyl propionate. The autoclave was flushed with CO and subsequently pressurized to 40 bar with an equimolar mixture of ethene and CO. The temperature was increased to 115° C. After 1 hour heating was stopped. At ambient temperature, the autoclave was depressurized and discharged. Analysis by means of gas chromatography showed that methyl propionate was formed with a selectivity of 95% at a methanol conversion of 60%. The reaction rate was approximately 1000 mol propionate per mol palladium per hour.

To this mixture 20 mmol POP, dissolved in 25 g methanol, was added. The solution was then stirred under nitrogen during 0.5 h. Subsequently the formed palladium/POP complex was extracted with water (150 g). Palladium recovery in the aqueous phase amounted to 97%. To this aqueous phase 50 g toluene, 10 g of triphenylphosphine and 1 g methanesulphonic acid were added. This mixture was heated in an autoclave under 5 bar CO pressure and 75° C. This temperature was maintained during 4 hours (simultaneous application of steps 1, 2 and 3). After cooling to ambient temperature and depressurizing, the autoclave was discharged. The mixture was drawn into a separatory funnel and after a settling time of 0.5 h the phases were separated (step 4). The organic extract phase (having a light yellow colour being an indication for the formed palladium-triphenylphosphine complex) was washed with water (25 ml). Palladium analysis of the organic extract phase and the aqueous raffinate phase revealed that the recovery in the organic extract phase was 95%. This organic extract phase was reused as a catalyst solution in an ethene carbonylation experiment under the same conditions as described hereinbefore. Catalyst activity amounted to 500 mol of propionate per gram-atom palladium per hour.

We claim:

1. A process comprising recovering a transition metal from an aqueous solution containing a complex of said transition metal with a cyclic phosphite having a bridgehead phosphorus atom linked to three oxygen atoms at least two of which form together with the bridgehead phosphorus atom part of a ring, said cyclic phosphite having a hydroxymethyl group linked to a ring carbon atom, by:
    (a) hydrolyzing the cyclic phosphite in said complex, thereby forming a reaction mixture, (b) contacting the reaction mixture obtained in step (a) with a compound forming a water-stable complex with said transition metal which is sufficiently water-stable to preclude the need to distill off water in order to achieve substantially complete recovery of said transition metal.

(c) contacting the reaction mixture obtained in step (b) with an organic extraction agent for said water-stable complex, thereby forming an organic extract phase containing at least a portion of said transition metal, and an aqueous raffinate phase, and (d) separating said organic extract phase containing at least a portion of said transition metal from said aqueous raffinate phase.

2. The process of claim 1 wherein said cyclic phosphite is a bicyclic phosphite having a general formula I:

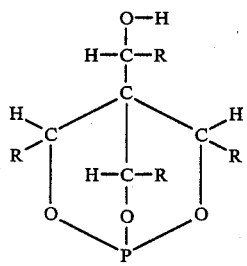

in which each R individually represents a hydrogen atom or an alkyl group having not more than three carbon atoms.

3. The process of claim 2 in wherein said bicyclic phosphite is 4-hydroxymethyl-2,6,7-trioxa-1-phosphabicyclo[2,2,2]octane.

4. The process of claim 1 wherein said hydrolysis is carried out in the presence of a protonic acid.

5. The process of claim 1 wherein said compound forming a water-stable complex with said transition metal is a compound of trivalent phosphorus.

6. The process of claim 5 wherein said component of trivalent phosphorus is a tertiary phosphine.

7. The process of claim 5 wherein said compound of trivalent phosphorus is a compound having a general formula:

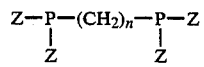

in which each Z individually represents a substituted or unsubstituted hydrocarbon group and n is an integer in the range of from 1 to 6.

8. The process of claim 1 wherein steps (a) and (b) are carried out simultaneously, said cyclic phosphite being hydrolyzed in the presence of said compound forming a water-stable complex with the transition metal.

9. The process of claim 1 wherein steps (a), (b) and (c) are carried out simultaneously.

10. The process of claim 1 wherein said transition metal is a metal selected from Group VIII of the Periodic Table of the Elements.

11. The process of claim 10 wherein said metal from Group VIII is a noble metal.

12. The process claim 11 wherein said noble metal is palladium.

13. The process of claim 11 wherein said noble metal is rhodium.

14. The process of claim 10 wherein said metal from Group VIII is cobalt.

* * * * *